(12) United States Patent
Khouengboua et al.

(10) Patent No.: US 10,433,957 B2
(45) Date of Patent: *Oct. 8, 2019

(54) STENT CELL BRIDGE FOR CUFF ATTACHMENT

(71) Applicant: St. Jude Medical, Cardiology Division, Inc., St. Paul, MN (US)

(72) Inventors: Sounthara (OTT) Khouengboua, Chaska, MN (US); Thomas Mark Benson, Minneapolis, MN (US); Xue Mei Li, Shoreview, MN (US)

(73) Assignee: St. Jude Medical, Cardiology Division, Inc., St. Paul, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/816,134

(22) Filed: Nov. 17, 2017

(65) Prior Publication Data

US 2018/0071090 A1    Mar. 15, 2018

Related U.S. Application Data

(63) Continuation of application No. 14/734,586, filed on Jun. 9, 2015, now Pat. No. 9,855,140.
(Continued)

(51) Int. Cl.
*A61F 2/24* (2006.01)

(52) U.S. Cl.
CPC .......... *A61F 2/2418* (2013.01); *A61F 2/2412* (2013.01); *A61F 2250/0039* (2013.01); *A61F 2250/0069* (2013.01)

(58) Field of Classification Search
None
See application file for complete search history.

(56) References Cited

U.S. PATENT DOCUMENTS 3,657,744 A    4/1972    Ersek
4,275,469 A    6/1981    Gabbay
(Continued)

FOREIGN PATENT DOCUMENTS

AU    2011202175 B1    7/2011
DE    19857887 A1    7/2000
(Continued)

OTHER PUBLICATIONS

Ruiz, Carlos, Overview of PRE-CE Mark Transcatheter Aortic Valve Technologies, Euro PCR, dated May 25, 2010.
(Continued)

*Primary Examiner* — Megan Y Wolf
(74) *Attorney, Agent, or Firm* — Lerner, David, Littenberg, Krumholz & Mentlik, LLP

(57) ABSTRACT

A prosthetic heart valve includes a collapsible stent extending from an inflow end to an outflow end, and a cuff having an inflow end an outflow end. The stent includes first and second circumferential rows of cells defined by first and second pluralities of struts, respectively. The second circumferential row is positioned closer to the outflow end of the stent than the first circumferential row. At least one cell in the second circumferential row includes by a first strut opposed to a fourth strut and a second strut opposed to a third strut. A bridging feature in at least one cell in the second circumferential row includes first and second supplemental struts extending across an intermediate portion of the cell. The outflow end of the cuff is coupled to the stent along the bridging feature.

19 Claims, 7 Drawing Sheets

Related U.S. Application Data

(60) Provisional application No. 62/009,989, filed on Jun. 10, 2014.

(56) References Cited

U.S. PATENT DOCUMENTS

| | | |
|---|---|---|
| 4,491,986 A | 1/1985 | Gabbay |
| 4,759,758 A | 7/1988 | Gabbay |
| 4,878,906 A | 11/1989 | Lindemann et al. |
| 4,922,905 A | 5/1990 | Strecker |
| 4,994,077 A | 2/1991 | Dobben |
| 5,078,720 A | 1/1992 | Burton et al. |
| 5,391,172 A | 2/1995 | Williams et al. |
| 5,411,552 A | 5/1995 | Andersen et al. |
| 5,415,664 A | 5/1995 | Pinchuk |
| 5,456,667 A | 10/1995 | Ham et al. |
| 5,480,423 A | 1/1996 | Ravenscroft et al. |
| 5,484,444 A | 1/1996 | Braunschweiler et al. |
| 5,702,418 A | 12/1997 | Ravenscroft |
| 5,824,041 A | 10/1998 | Lenker et al. |
| 5,843,167 A | 12/1998 | Dwyer et al. |
| 5,855,601 A | 1/1999 | Bessler et al. |
| 5,935,163 A | 8/1999 | Gabbay |
| 5,961,549 A | 10/1999 | Nguyen et al. |
| 5,980,533 A | 11/1999 | Holman |
| 6,077,297 A | 6/2000 | Robinson et al. |
| 6,083,257 A | 7/2000 | Taylor et al. |
| 6,090,140 A | 7/2000 | Gabbay |
| 6,214,036 B1 | 4/2001 | Letendre et al. |
| 6,264,691 B1 | 7/2001 | Gabbay |
| 6,267,783 B1 | 7/2001 | Letendre et al. |
| 6,269,819 B1 | 8/2001 | Oz et al. |
| 6,368,348 B1 | 4/2002 | Gabbay |
| 6,391,050 B1 | 5/2002 | Broome |
| 6,419,695 B1 | 7/2002 | Gabbay |
| 6,458,153 B1 | 10/2002 | Bailey et al. |
| 6,468,299 B2 | 10/2002 | Stack et al. |
| 6,468,660 B2 | 10/2002 | Ogle et al. |
| 6,488,702 B1 | 12/2002 | Besselink |
| 6,517,576 B2 | 2/2003 | Gabbay |
| 6,533,810 B2 | 3/2003 | Hankh et al. |
| 6,582,464 B2 | 6/2003 | Gabbay |
| 6,610,088 B1 | 8/2003 | Gabbay |
| 6,623,518 B2 | 9/2003 | Thompson et al. |
| 6,685,625 B2 | 2/2004 | Gabbay |
| 6,719,789 B2 | 4/2004 | Cox |
| 6,730,118 B2 | 5/2004 | Spenser et al. |
| 6,736,845 B2 | 5/2004 | Marquez et al. |
| 6,783,556 B1 | 8/2004 | Gabbay |
| 6,790,230 B2 | 9/2004 | Beyersdorf et al. |
| 6,814,746 B2 | 11/2004 | Thompson et al. |
| 6,830,584 B1 | 12/2004 | Seguin |
| 6,869,444 B2 | 3/2005 | Gabbay |
| 6,893,460 B2 | 5/2005 | Spenser et al. |
| 6,908,481 B2 | 6/2005 | Cribier |
| 7,018,406 B2 | 3/2006 | Seguin et al. |
| 7,025,780 B2 | 4/2006 | Gabbay |
| 7,137,184 B2 | 11/2006 | Schreck |
| 7,160,322 B2 | 1/2007 | Gabbay |
| 7,247,167 B2 | 7/2007 | Gabbay |
| 7,267,686 B2 | 9/2007 | DiMatteo et al. |
| 7,311,730 B2 | 12/2007 | Gabbay |
| 7,329,278 B2 | 2/2008 | Seguin et al. |
| 7,374,573 B2 | 5/2008 | Gabbay |
| 7,381,218 B2 | 6/2008 | Schreck |
| 7,399,315 B2 | 7/2008 | Iobbi |
| 7,452,371 B2 | 11/2008 | Pavcnik et al. |
| 7,476,244 B2 | 1/2009 | Buzzard et al. |
| 7,510,572 B2 | 3/2009 | Gabbay |
| 7,524,331 B2 | 4/2009 | Birdsall |
| RE40,816 E | 6/2009 | Taylor et al. |
| 7,585,321 B2 | 9/2009 | Cribier |
| 7,682,390 B2 | 3/2010 | Seguin |
| 7,731,742 B2 | 6/2010 | Schlick et al. |
| 7,803,185 B2 | 9/2010 | Gabbay |
| 7,846,203 B2 | 12/2010 | Cribier |
| 7,846,204 B2 | 12/2010 | Letac et al. |
| 7,914,569 B2 | 3/2011 | Nguyen et al. |
| D648,854 S | 11/2011 | Braido |
| D652,926 S | 1/2012 | Braido |
| D652,927 S | 1/2012 | Braido et al. |
| D653,341 S | 1/2012 | Braido et al. |
| D653,342 S | 1/2012 | Braido et al. |
| D653,343 S | 1/2012 | Ness et al. |
| D654,169 S | 2/2012 | Braido |
| D654,170 S | 2/2012 | Braido et al. |
| D660,432 S | 5/2012 | Braido |
| D660,433 S | 5/2012 | Braido et al. |
| D660,967 S | 5/2012 | Braido et al. |
| 8,313,525 B2 | 11/2012 | Tuval et al. |
| 8,353,955 B2 | 1/2013 | Styrc et al. |
| 8,568,475 B2 | 10/2013 | Nguyen et al. |
| 9,855,140 B2 * | 1/2018 | Khouengboua ....... A61F 2/2412 |
| 2002/0036220 A1 | 3/2002 | Gabbay |
| 2002/0183827 A1 | 12/2002 | Derus et al. |
| 2003/0023303 A1 | 1/2003 | Palmaz et al. |
| 2003/0050694 A1 | 3/2003 | Yang et al. |
| 2003/0130726 A1 | 7/2003 | Thorpe et al. |
| 2003/0144725 A1 | 7/2003 | Lombardi |
| 2004/0039436 A1 | 2/2004 | Spenser et al. |
| 2004/0049262 A1 | 3/2004 | Obermiller et al. |
| 2004/0093075 A1 | 5/2004 | Kuehne |
| 2004/0148009 A1 | 7/2004 | Buzzard et al. |
| 2004/0186563 A1 | 9/2004 | Lobbi |
| 2004/0210304 A1 | 10/2004 | Seguin et al. |
| 2004/0260390 A1 | 12/2004 | Sarac et al. |
| 2005/0004583 A1 | 1/2005 | Oz et al. |
| 2005/0049667 A1 | 3/2005 | Arbefeuille et al. |
| 2005/0096726 A1 | 5/2005 | Sequin et al. |
| 2005/0137688 A1 | 6/2005 | Salahieh et al. |
| 2005/0137695 A1 | 6/2005 | Salahieh et al. |
| 2005/0137697 A1 | 6/2005 | Salahieh et al. |
| 2005/0240200 A1 | 10/2005 | Bergheim |
| 2005/0256566 A1 | 11/2005 | Gabbay |
| 2006/0008497 A1 | 1/2006 | Gabbay |
| 2006/0025857 A1 | 2/2006 | Bergheim et al. |
| 2006/0058872 A1 | 3/2006 | Salahieh et al. |
| 2006/0074484 A1 | 4/2006 | Huber |
| 2006/0122692 A1 | 6/2006 | Gilad et al. |
| 2006/0149360 A1 | 7/2006 | Schwammenthal et al. |
| 2006/0173532 A1 | 8/2006 | Flagle et al. |
| 2006/0178740 A1 | 8/2006 | Stacchino et al. |
| 2006/0195180 A1 | 8/2006 | Kheradvar et al. |
| 2006/0206202 A1 | 9/2006 | Bonhoeffer et al. |
| 2006/0241744 A1 | 10/2006 | Beith |
| 2006/0241745 A1 | 10/2006 | Solem |
| 2006/0259120 A1 | 11/2006 | Vongphakdy et al. |
| 2006/0259136 A1 | 11/2006 | Nguyen et al. |
| 2006/0259137 A1 | 11/2006 | Artof et al. |
| 2006/0265056 A1 | 11/2006 | Nguyen et al. |
| 2006/0276813 A1 | 12/2006 | Greenberg |
| 2006/0282150 A1 | 12/2006 | Olson et al. |
| 2006/0282157 A1 | 12/2006 | Hill et al. |
| 2007/0010876 A1 | 1/2007 | Salahieh et al. |
| 2007/0027534 A1 | 2/2007 | Bergheim et al. |
| 2007/0043435 A1 | 2/2007 | Seguin et al. |
| 2007/0055358 A1 | 3/2007 | Krolik et al. |
| 2007/0067029 A1 | 3/2007 | Gabbay |
| 2007/0093890 A1 | 4/2007 | Eliasen et al. |
| 2007/0100435 A1 | 5/2007 | Case et al. |
| 2007/0118210 A1 | 5/2007 | Pinchuk |
| 2007/0156225 A1 | 7/2007 | George et al. |
| 2007/0213813 A1 | 9/2007 | Von Segesser et al. |
| 2007/0233228 A1 | 10/2007 | Eberhardt et al. |
| 2007/0244545 A1 | 10/2007 | Birdsall et al. |
| 2007/0244552 A1 | 10/2007 | Salahieh et al. |
| 2007/0260301 A1 | 11/2007 | Chuter et al. |
| 2007/0288087 A1 | 12/2007 | Fearnot et al. |
| 2008/0004688 A1 | 1/2008 | Spenser et al. |
| 2008/0009940 A1 | 1/2008 | Cribier |
| 2008/0021552 A1 | 1/2008 | Gabbay |
| 2008/0039934 A1 | 2/2008 | Styrc |
| 2008/0071369 A1 | 3/2008 | Tuval et al. |
| 2008/0082164 A1 | 4/2008 | Friedman |
| 2008/0097595 A1 | 4/2008 | Gabbay |

(56) References Cited

U.S. PATENT DOCUMENTS

| | | |
|---|---|---|
| 2008/0114452 A1 | 5/2008 | Gabbay |
| 2008/0125853 A1 | 5/2008 | Bailey et al. |
| 2008/0140189 A1 | 6/2008 | Nguyen et al. |
| 2008/0147179 A1 | 6/2008 | Cai et al. |
| 2008/0147183 A1 | 6/2008 | Styrc |
| 2008/0154355 A1 | 6/2008 | Benichou et al. |
| 2008/0154356 A1 | 6/2008 | Obermiller et al. |
| 2008/0228264 A1 | 9/2008 | Li et al. |
| 2008/0243245 A1 | 10/2008 | Thambar et al. |
| 2008/0255662 A1 | 10/2008 | Stacchino et al. |
| 2008/0262602 A1 | 10/2008 | Wilk et al. |
| 2008/0269878 A1 | 10/2008 | Iobbi |
| 2008/0269879 A1 | 10/2008 | Sathe et al. |
| 2009/0112309 A1 | 4/2009 | Jaramillo et al. |
| 2009/0118826 A1 | 5/2009 | Khaghani |
| 2009/0138079 A1 | 5/2009 | Tuval et al. |
| 2009/0240320 A1 | 9/2009 | Tuval et al. |
| 2009/0287299 A1 | 11/2009 | Tabor et al. |
| 2010/0004740 A1 | 1/2010 | Seguin et al. |
| 2010/0036484 A1 | 2/2010 | Hariton et al. |
| 2010/0049306 A1 | 2/2010 | House et al. |
| 2010/0049313 A1 | 2/2010 | Alon et al. |
| 2010/0082094 A1 | 4/2010 | Quadri et al. |
| 2010/0087907 A1 | 4/2010 | Lattouf |
| 2010/0114305 A1 | 5/2010 | Kang et al. |
| 2010/0121434 A1 | 5/2010 | Paul et al. |
| 2010/0131055 A1 | 5/2010 | Case et al. |
| 2010/0168778 A1 | 7/2010 | Braido |
| 2010/0168839 A1 | 7/2010 | Braido et al. |
| 2010/0185277 A1 | 7/2010 | Braido et al. |
| 2010/0191326 A1 | 7/2010 | Alkhatib |
| 2010/0204781 A1 | 8/2010 | Alkhatib |
| 2010/0204785 A1 | 8/2010 | Alkhatib |
| 2010/0217382 A1 | 8/2010 | Chau et al. |
| 2010/0249911 A1 | 9/2010 | Alkhatib |
| 2010/0249923 A1 | 9/2010 | Alkhatib et al. |
| 2010/0286768 A1 | 11/2010 | Alkhatib |
| 2010/0298931 A1 | 11/2010 | Quadri et al. |
| 2011/0029072 A1 | 2/2011 | Gabbay |
| 2011/0208298 A1 | 8/2011 | Tuval et al. |
| 2011/0282425 A1 | 11/2011 | Dwork |
| 2012/0071969 A1 | 3/2012 | Li et al. |
| 2012/0089223 A1 | 4/2012 | Nguyen et al. |
| 2012/0197391 A1 | 8/2012 | Alkhatib et al. |
| 2013/0079869 A1 | 3/2013 | Straubinger et al. |
| 2013/0274873 A1* | 10/2013 | Delaloye ............. A61F 2/2409 623/2.18 |
| 2014/0243966 A1 | 8/2014 | Garde et al. |
| 2014/0277411 A1* | 9/2014 | Bortlein ............. A61F 2/24 623/2.11 |
| 2016/0038281 A1 | 2/2016 | Delaloye et al. |

FOREIGN PATENT DOCUMENTS

| | | |
|---|---|---|
| DE | 20000659 U1 | 5/2001 |
| DE | 10121210 A1 | 11/2002 |
| DE | 102005003632 A1 | 8/2006 |
| DE | 202008009610 U1 | 12/2008 |
| EP | 0850607 A1 | 7/1998 |
| EP | 1000590 A1 | 5/2000 |
| EP | 1360942 A1 | 11/2003 |
| EP | 1584306 A1 | 10/2005 |
| EP | 1598031 A2 | 11/2005 |
| EP | 1872743 A1 | 1/2008 |
| EP | 1926455 A2 | 6/2008 |
| FR | 2850008 A1 | 7/2004 |
| FR | 2847800 B1 | 10/2005 |
| JP | 2010523234 | 7/2010 |
| JP | 2010528761 A | 8/2010 |
| JP | 2010540079 A | 12/2010 |
| JP | 2011512922 | 4/2011 |
| WO | 9117720 A1 | 11/1991 |
| WO | 9716133 A1 | 5/1997 |
| WO | 9832412 A2 | 7/1998 |
| WO | 9913801 A1 | 3/1999 |
| WO | 0069368 A2 | 11/2000 |
| WO | 0128459 A1 | 4/2001 |
| WO | 0149213 A2 | 7/2001 |
| WO | 0154625 A1 | 8/2001 |
| WO | 0156500 A2 | 8/2001 |
| WO | 0176510 A2 | 10/2001 |
| WO | 0236048 A1 | 5/2002 |
| WO | 0247575 A2 | 6/2002 |
| WO | 02067782 A2 | 9/2002 |
| WO | 03047468 A1 | 6/2003 |
| WO | 2005070343 A1 | 8/2005 |
| WO | 06073626 A2 | 7/2006 |
| WO | 07071436 A2 | 6/2007 |
| WO | 2008042266 A2 | 4/2008 |
| WO | 08070797 A2 | 6/2008 |
| WO | 2008125153 A1 | 10/2008 |
| WO | 2008138584 A1 | 11/2008 |
| WO | 2008150529 A1 | 12/2008 |
| WO | 2009029199 A1 | 3/2009 |
| WO | 2009042196 A2 | 4/2009 |
| WO | 2009091509 A1 | 7/2009 |
| WO | 2010008548 A2 | 1/2010 |
| WO | 2010008549 A1 | 1/2010 |
| WO | 2010096176 A1 | 8/2010 |
| WO | 2010098857 A1 | 9/2010 |
| WO | 2012026965 A2 | 3/2012 |
| WO | 2012036741 A2 | 3/2012 |

OTHER PUBLICATIONS

Quaden, Rene, et al., Percutaneous aortic valve replacement: resection before implantation, 836-840,European J. of Cardio-thoracic Surgery, 27 (2005).

Knudsen, L.L., et al., Catheter-implanted prosthetic heart valves, The International Journal of Artificial Organs, vol. 16, No. 5 1993, pp. 253-262.

Moazami, Nader, et al., Transluminal Aortic Valve Placement, Moazami, ASAIO Journal, 1996; 42:M381-M385.

Andersen, Henning Rud, Transluminal Catheter Implanted Prosthetic Heart Valves, International Journal of Angiology 7:102-106 (1998).

Andersen, H. R., et al., Transluminal implantation of artificial heart valves, European Heart Journal (1992) 13, 704-708.

Zegdi, Rachid, MD, PhD et al., Is It Reasonable to Treat All Calcified Stenotic Aortic Valves With a Valved Stent?, 579-584, J. of the American College of Cardiology, vol. 51, No. 5, Feb. 5, 2008.

U.S. Appl. No. 29/375,243, filed Sep. 20, 2010.

U.S. Appl. No. 29/375,260, filed Sep. 20, 2010.

European Search Report for Application No. EP 14171169.4 dated Oct. 7, 2015.

International Search Report and Written Opnion for Aplication No. PCT/US2011/001615 dated Jul. 11, 2012.

Commonly owned co-pending U.S. Appl. No. 13/216,124, filed Aug. 23, 2011.

International Search Report Application No. PCT/US2011/048963, dated Dec. 15, 2011.

International Search Report Application No. PCT/US2011/048989, dated Dec. 15, 2011.

International Search Report Application No. PCT/US2011/048967, dated Dec. 15, 2011.

International Search Report for Application No. PCT/US2011/001597 dated Mar. 7, 2012.

Commonly owned co-pending U.S. Appl. No. 13/234,782, filed Sep. 16, 2011.

Commonly owned co-pending U.S. Appl. No. 13/788,820, filed Mar. 7, 2013.

Commonly owned co-pending U.S. Appl. No. 13/212,442, filed Aug. 18, 2011.

International Search Report for Application No. PCT/US2011/001450 dated Mar. 5, 2012.

Australian Examination Report for Application No. 2011293898 dated Jul. 26, 2013.

(56) References Cited

OTHER PUBLICATIONS

International Search Report and Written Opinion for Application No. PCT/US2013/039407 dated Feb. 10, 2014.

Walther et al., "Transapical approach for sutureless stent-fixed aortic valve implantation: experimental results"; European Journal of Cardio-thoracic Surgery 29 (2006) 703-708 (Jan. 30, 2006).

Todd M. Dewey et al., "Transapical aortic valve implantation: an animal feasibility study"; The annals of thoracic surgery 2006; 82: 110-116 (Feb. 13, 2006).

Samuel V. Lichtenstein et al., "Transapical Transcatheter Aortic Valve Implantation in Humans", Circulation. 2006; 114: 591-596 (Jul. 31, 2006).

Christoph H. Huber, et al., "Direct-Access Valve Replacement", Journal of the American College of Cardiology, vol. 46 No. 2, pp. 366-370, (Jul. 19, 2005).

M. J. Mack, "Minimally invasive cardiac surgery", Surgical Endoscopy, 2006, 20:S488-S492, DOI: 10.1007/s00464-006-0110-8 (presented Apr. 24, 2006).

John G. Webb et al., "Percutaneous Aortic Valve Implantation Retrograde From the Femoral Artery", Circulation, 2006; 113:842-850 (Feb. 6, 2006).

Samuel V. Lichtenstein, "Closed heart surgery: Back to the future", The Journal of Thoracic and Cardiovascular Surgery, vol. 131, No. 5, pp. 941-943, May 2006.

Textbook "Transcatheter Valve Repair", 2006, pp. 165-186.

\* cited by examiner

STENT CELL BRIDGE FOR CUFF ATTACHMENT

CROSS-REFERENCE TO RELATED APPLICATIONS

The present application is a continuation of U.S. patent application Ser. No. 14/734,586, filed Jun. 9, 2015 and issued as U.S. Pat. No. 9,855,140, which claims the benefit of the filing date of U.S. Provisional Patent application No. 62/009,989 filed Jun. 10, 2014, the disclosures of which are both hereby incorporated by reference herein.

BACKGROUND

The present disclosure relates in general to heart valve replacement and, in particular, to collapsible prosthetic heart valves. More particularly, the present disclosure relates to devices and methods for positioning collapsible prosthetic heart valves and sealing same in a patient's anatomy to minimize or prevent paravalvular leakage and increase coronary perfusion.

Prosthetic heart valves that are collapsible to a relatively small circumferential size can be delivered into a patient less invasively than valves that are not collapsible. For example, a collapsible valve may be delivered into a patient via a tube-like delivery apparatus such as a catheter, a trocar, a laparoscopic instrument, or the like. This collapsibility can avoid the need for a more invasive procedure such as full open-chest, open-heart surgery.

Collapsible prosthetic heart valves typically take the form of a valve structure mounted on a stent. There are two types of stents on which the valve structures are ordinarily mounted: a self-expanding stent or a balloon-expandable stent. To place such valves into a delivery apparatus and ultimately into a patient, the valve must first be collapsed or crimped to reduce its circumferential size.

When a collapsed prosthetic valve has reached the desired implant site in the patient (e.g., at or near the annulus of the patient's native heart valve that is to be replaced by the prosthetic valve), the prosthetic valve can be deployed or released from the delivery apparatus and re-expanded to full operating size. For balloon-expandable valves, this generally involves releasing the entire valve, and then expanding a balloon positioned within the valve stent. For self-expanding valves, on the other hand, the stent automatically expands as the sheath covering the valve is withdrawn.

BRIEF SUMMARY

In one embodiment of the disclosure, a prosthetic heart valve includes a stent and a cuff. The stent has a collapsed condition and an expanded condition and extends from an inflow end to an outflow end. The stent includes a first circumferential row of cells defined by a first plurality of struts and a second circumferential row of cells defined by a second plurality of struts. The second circumferential row is positioned closer to the outflow end of the stent than the first circumferential row. At least one cell in the second circumferential row includes a first strut opposed to a fourth strut and a second strut opposed to a third strut, the first and fourth struts being connected to the second and third struts. A bridging feature in at least one cell in the second circumferential row includes a first supplemental strut having a first end and a second end, and a second supplemental strut having a first end and a second end. The first end of the first supplemental strut is attached to at least one of the first and third struts, the second end of the first supplemental strut is attached to the first end of the second supplemental strut, and the second end of the second supplemental strut is attached to at least one of the second and fourth struts. The cuff has an inflow end and an outflow end. The outflow end of the cuff is coupled to the stent along the bridging feature.

In another embodiment of the disclosure, a method of implanting a prosthetic heart valve into a native valve annulus includes providing a prosthetic heart valve including a stent and a cuff attached to the stent. The stent extends from an inflow end to an outflow end and has a collapsed condition, an expanded condition, a first circumferential row of cells, and a second circumferential row of cells. The cuff has an outflow end attached to at least one bridging feature extending across an intermediate portion of one of the cells in the second circumferential row. The method may also include delivering the prosthetic heart valve to a site of implantation in the collapsed condition and deploying the prosthetic heart valve at the site of implantation. When in the expanded condition, a portion of the first circumferential row of cells may be in contact with the native valve annulus and a portion of the second circumferential row of cells may be adjacent a coronary artery ostium.

BRIEF DESCRIPTION OF THE DRAWINGS

Various embodiments of the present disclosure are described herein with reference to the drawings, wherein.

Various embodiments of the present invention are described with reference to the appended drawings. It is to be appreciated that these drawings depict only some embodiments of the invention and are therefore not to be considered limiting of its scope.

DETAILED DESCRIPTION

The successful functioning of a prosthetic heart valve may be dependent on multiple factors including accurate deployment and effective sealing within the patient's anatomy. Inaccurate placement and/or anchoring may result in the leakage of blood between the implanted heart valve and the native valve annulus, commonly referred to as paravalvular or perivalvular leakage ("PV leakage"). In aortic valves, PV leakage enables blood flow from the aorta back into the left ventricle, which may reduce cardiac efficiency and put a greater strain on the heart muscle. Additionally, calcification of the aortic valve may affect performance, and the interaction between the implanted valve and the calcified tissue is believed to be relevant to PV leakage.

Moreover, anatomical variations between patients may require removal of a fully deployed heart valve from the patient if it appears that the valve is not functioning properly. Removing a fully deployed heart valve increases the length of the procedure and increases the risk of infection and/or damage to heart tissue. Thus, methods and devices are desirable that would reduce the need to remove a deployed valve. Methods and devices are also desirable that would reduce the likelihood of PV leakage around the implanted heart valve.

As used herein, the term "outflow end," when used in connection with a prosthetic heart valve, refers to the end of the heart valve from which blood exits when working in an intended manner, whereas the term "inflow end," when used in connection with a prosthetic heart valve, refers to the end of the heart valve into which blood enters when working in an intended manner. Also as used herein, the terms "generally," "substantially," and "about" are intended to mean that slight deviations from absolute are included within the scope of the term so modified.

Figure 1:
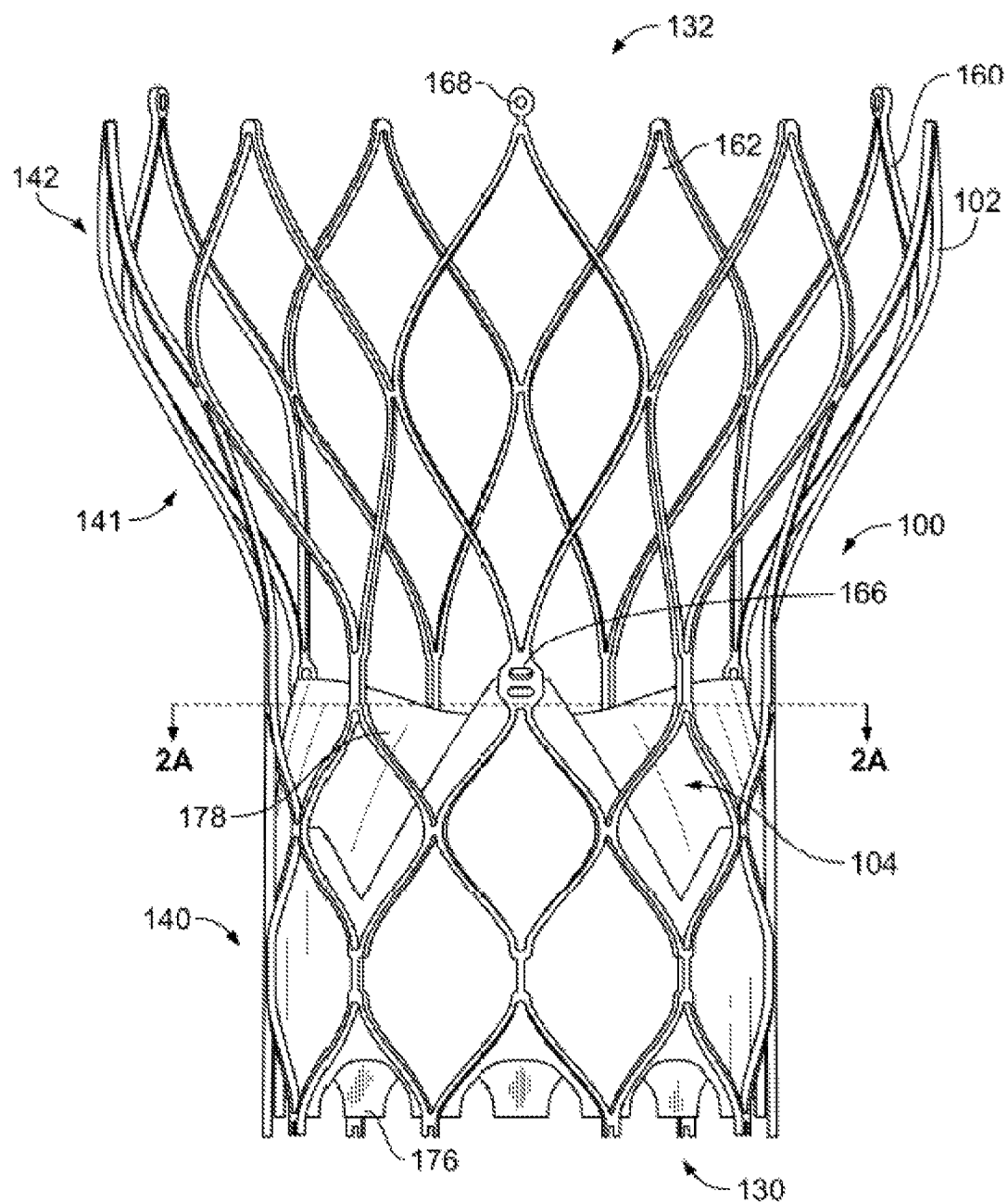
FIG. 1 is a side elevational view of a collapsible prosthetic heart valve known in the art.

FIG. 1 shows a collapsible stent-supported prosthetic heart valve 100 including a stent 102 and a valve assembly 104 as known in the art. Prosthetic heart valve 100 is designed to replace a native tricuspid valve of a patient, such as a native aortic valve. It should be noted that, while portions of the current disclosure are described predominantly in connection with their application to a prosthetic aortic valve and a stent having a shape as illustrated in FIG. 1, the disclosure is also applicable to other valves and stents. For example, the valve could be another type of valve besides an aortic valve, such as a bicuspid valve, including the mitral valve, and the stent could have different shapes, such as a flared or conical annulus section, a less bulbous aortic section, a differently shaped transition section, and the like.

Stent 102 of prosthetic heart valve 100 may be formed from, for example, a shape memory material, such as the nickel-titanium alloy known as "Nitinol" or other suitable metals, and in particular, from those materials that are capable of self-expansion. Stent 102 extends from an inflow or annulus end 130 to an outflow or aortic end 132, and includes an annulus section 140 adjacent inflow end 130, an aortic section 142 adjacent outflow end 132, and a transition section 141 between annulus section 140 and aortic section 142. Annulus section 140 has a relatively small cross-section in the expanded condition, while aortic section 142 has a relatively large cross-section in the expanded condition. Preferably, annulus section 140 is in the form of a cylinder having a substantially constant diameter along its length. Transition section 141 may taper outwardly from annulus section 140 to aortic section 142. Each of the sections of stent 102 includes a plurality of struts 160 forming cells 162 connected to one another in one or more annular rows around stent 102. For example, as shown in FIG. 1, annulus section 140 may have two annular rows of complete cells 162, and aortic section 142 and transition section 141 may each have one or more annular rows of partial cells 162. Cells 162 in aortic section 142 may be larger than the cells in annulus section 140. The larger cells in aortic section 142 better enable prosthetic valve 100 to be positioned in the native valve architecture without the stent structure interfering with blood flow to the coronary arteries.

Stent 102 may also include a plurality of commissure features 166 for attaching the commissure between two adjacent leaflets to stent 102. Commissure features 166 may lie at the intersection of four cells 162, two of the cells being adjacent one another in the same annular row, and the other two cells being in different annular rows and lying in end-to-end relationship. Preferably, commissure features 166 are positioned entirely within annulus section 140 or at the juncture of annulus section 140 and transition section 141. Commissure features 166 may include one or more eyelets which facilitate the suturing of the leaflet commissure to stent 102.

Stent 102 may include one or more retaining elements 168 at distal end 132 thereof, retaining elements 168 being sized and shaped to cooperate with female retaining structures (not shown) provided on the device for deploying prosthetic heart valve 100. The engagement of retaining elements 168 with the female retaining structures on the deployment device helps maintain prosthetic heart valve 100 in assembled relationship with the deployment device, minimizes longitudinal movement of the prosthetic heart valve relative to the deployment device during unsheathing or resheathing procedures, and helps prevent rotation of the prosthetic heart valve relative to the deployment device as the deployment device is advanced to the target location and the heart valve deployed.

Valve assembly 104 is secured to stent 102, preferably within annulus section 140 of stent 102. Valve assembly 104 includes cuff 176 and a plurality of leaflets 178 which collectively function as a one-way valve by coapting with one another. As a prosthetic aortic valve, valve 100 has three leaflets 178, as well as three commissure features 166. However, it will be appreciated that other prosthetic heart valves having a greater or lesser number of leaflets 178 and commissure features 166 are possible.

Although cuff 176 is shown in FIG. 1 as being disposed on the luminal or inner surface of annulus section 140, it is contemplated that cuff 176 may be disposed on the abluminal or outer surface of annulus section 140 or may cover all or part of either or both of the luminal and abluminal surfaces. Both cuff 176 and leaflets 178 may be wholly or partly formed from any suitable biological material, such as porcine or bovine pericardial tissue, or from a polymer such as, for example, polytetrafluoroethylene, polyurethane, ultra-high molecular weight polyethylene, polyethylene terephthalate, polyester or suitable combinations thereof.

Prosthetic heart valve 100 may be used to replace a native aortic valve, a surgical heart valve or a heart valve that has undergone a surgical procedure. Prosthetic heart valve 100 may be delivered to the desired site (e.g., near the native aortic annulus) using any suitable delivery device. During delivery, prosthetic heart valve 100 is disposed inside the delivery device in the collapsed condition. The delivery device may be introduced into a patient using a transfemoral, transapical, transseptal or any other percutaneous approach. Once the delivery device has reached the target site, the user may deploy prosthetic heart valve 100. Upon deployment, prosthetic heart valve 100 expands so that annulus section 140 is in secure engagement within the native aortic annulus. When prosthetic heart valve 100 is properly positioned inside the heart, it works as a one-way valve, allowing blood to flow from the left ventricle of the heart to the aorta, and preventing blood from flowing in the opposite direction.

Figure 2A:
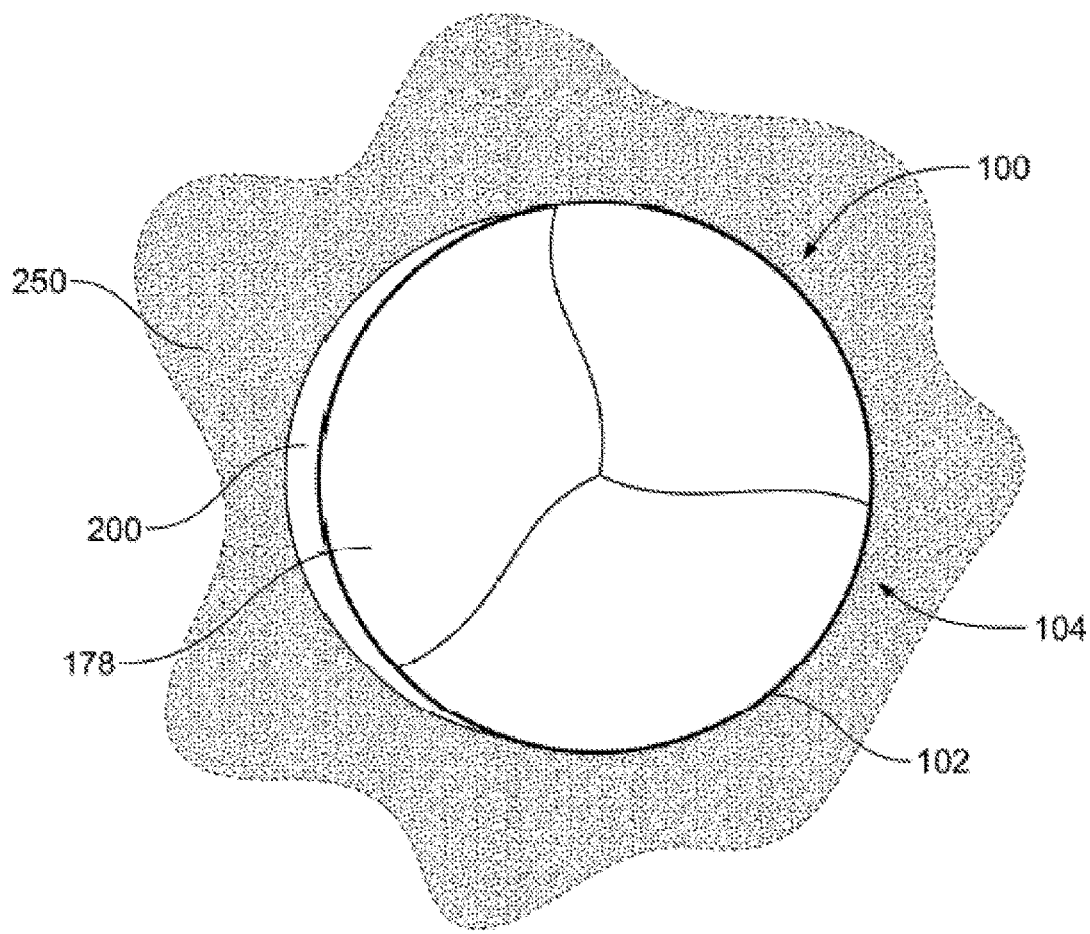
FIG. 2A is a highly schematic cross-sectional view taken along line 2A-2A of FIG. 1 and showing the prosthetic heart valve disposed within a native valve annulus.
Figure 2B:
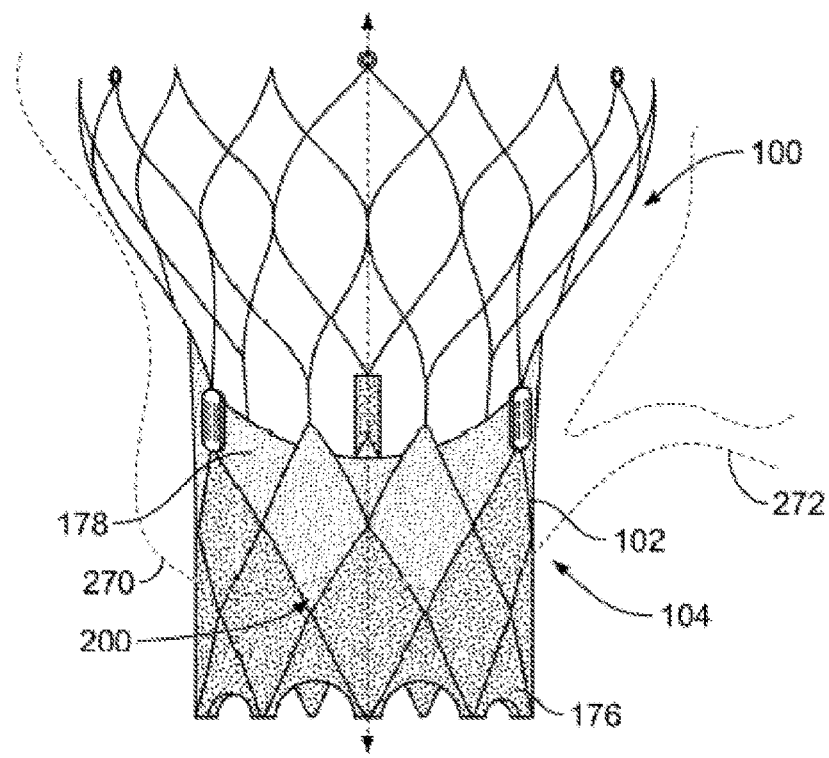
FIG. 2B is a side elevation view of a collapsible prosthetic heart valve after implantation.

FIG. 2A is a highly schematic cross-sectional illustration of prosthetic heart valve 100 disposed within native valve annulus 250. As seen in the figure, in some cases, stent 102 may be implanted in a slightly tilted position or disposed slightly away from the desired site within native valve annulus 250. Due to such imperfect placement, at certain locations around the perimeter of heart valve 100, potential gaps 200 may form between the heart valve and native valve annulus 250. Blood flowing through these gaps and around leaflets 178 of valve assembly 104 can cause regurgitation and other inefficiencies which reduce cardiac performance. Such improper fitment may also result from suboptimal native valve annulus geometry due, for example, to calcification of native valve annulus 250 or to unresected native leaflets. As shown in FIG. 2B, potential gaps 200 may also be formed between cuff 176 and aortic root 270. Coronary artery 272 is also shown schematically in order to appreciate the general location of potential gaps 200 with respect to nearby anatomy. It should be understood that the distance between stent 102 and the opening to a coronary artery 272 ("coronary ostium") may be larger or smaller than what is illustrated in FIG. 2B, and may include a situation in which stent 102 contacts tissue at the coronary ostium. In addition, prosthetic valve 100 may be positioned in rotational orientations other than that shown. As noted above, larger cells 162 in the transition section 141 and/or aortic section 142 may reduce the volume of structures adjacent each coronary ostium, limiting the obstruction of blood flowing into one or more coronary ostia.

Figure 2C:
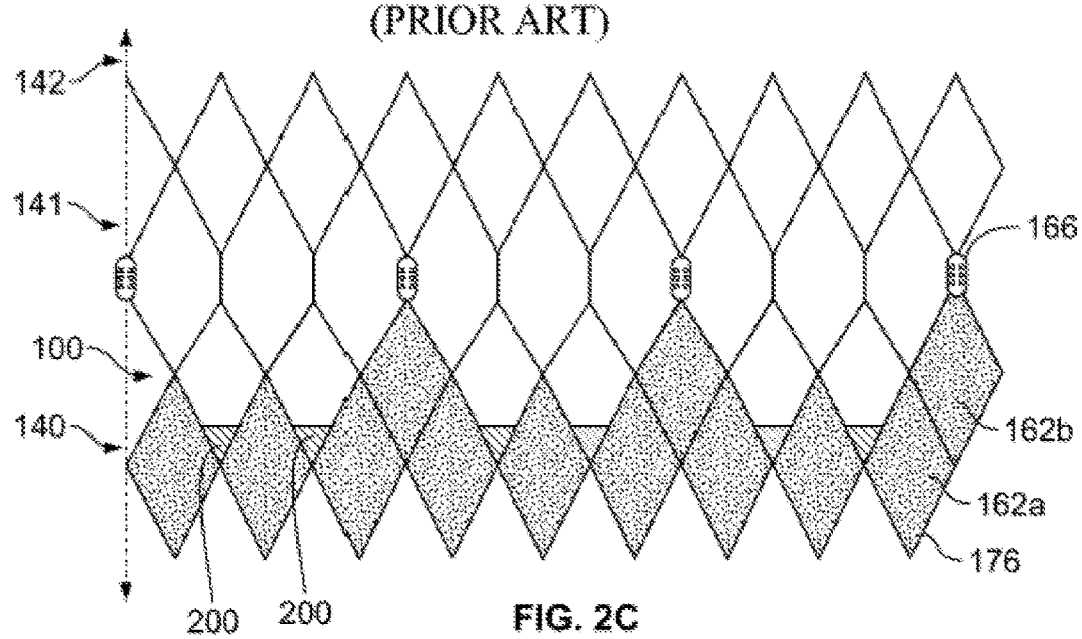
FIG. 2C is a developed view of a portion of the heart valve of FIG. 2B in an expanded condition.

In FIG. 2C, a developed view of a portion of heart valve 100 shows annulus section 140, transition section 141, and aortic section 142 of stent 102, commissure features 166 and cuff 176. For the sake of clarity, leaflets are not shown. The location of potential gaps 200 in relation to the cuff 176 is illustrated with hashed lines in FIG. 2C. It should be understood that the potential gaps 200 may be larger, smaller, or differently positioned depending on the particular positioning of the prosthetic valve 100 within the patient's anatomy, as well as the anatomy itself. As shown in FIG. 2C, cuff 176 generally spans the entirety of each cell 162*a* in a first row and the entirety of certain cells 162*b* in a second row, where the second row is positioned closer to the outflow end 132 than the first row. In the illustrated valve 100, the cuff 176 spans the entirety of three cells 162*b* in the second row adjacent commissure features 166.

Figure 3A:
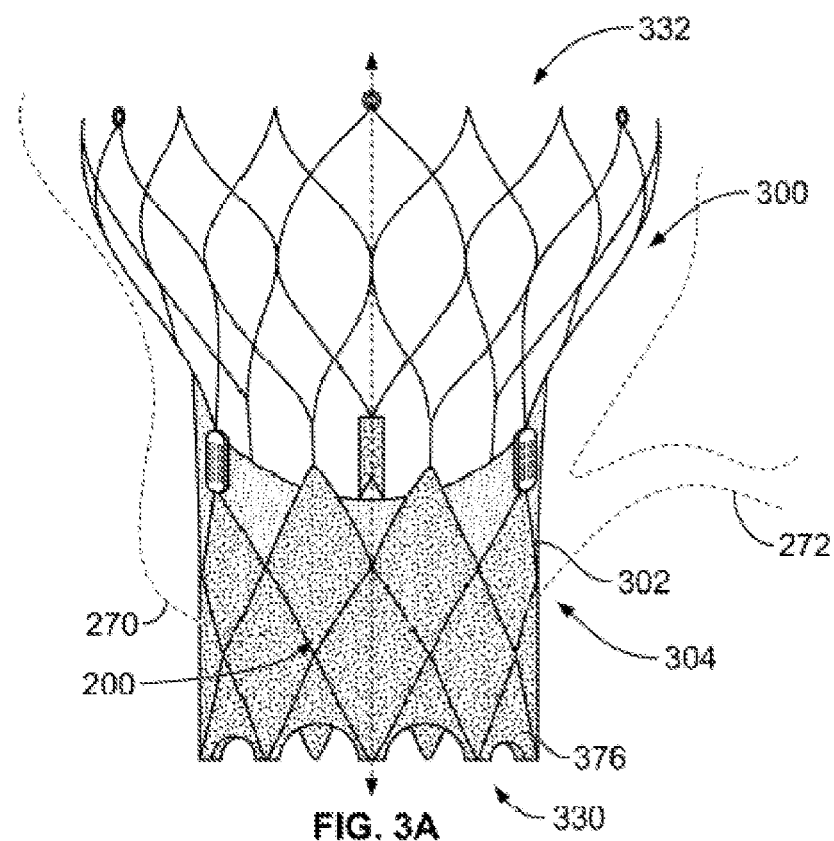
FIG. 3A is a side elevational view of a collapsible prosthetic heart valve according to another embodiment of the disclosure after implantation.

FIG. 3A illustrates one example of a collapsible stent-supported prosthetic heart valve 300 capable of reducing PV leakage. Heart valve 300 is identical in most respects to heart valve 100, with the exception that cuff 376 extends further in the outflow direction toward aortic section 342. For example, heart valve 300 includes stent 302 and valve assembly 304 disposed within stent 302. Stent 302 generally includes annulus section 340 adjacent inflow end 330, aortic section 342 adjacent outflow end 332, and transition section 341 between annulus action 340 and aortic section 342. Components of prosthetic heart valve 300 may be formed of the same materials as described above in connection with similar components of prosthetic valve 100.

Figure 3B:
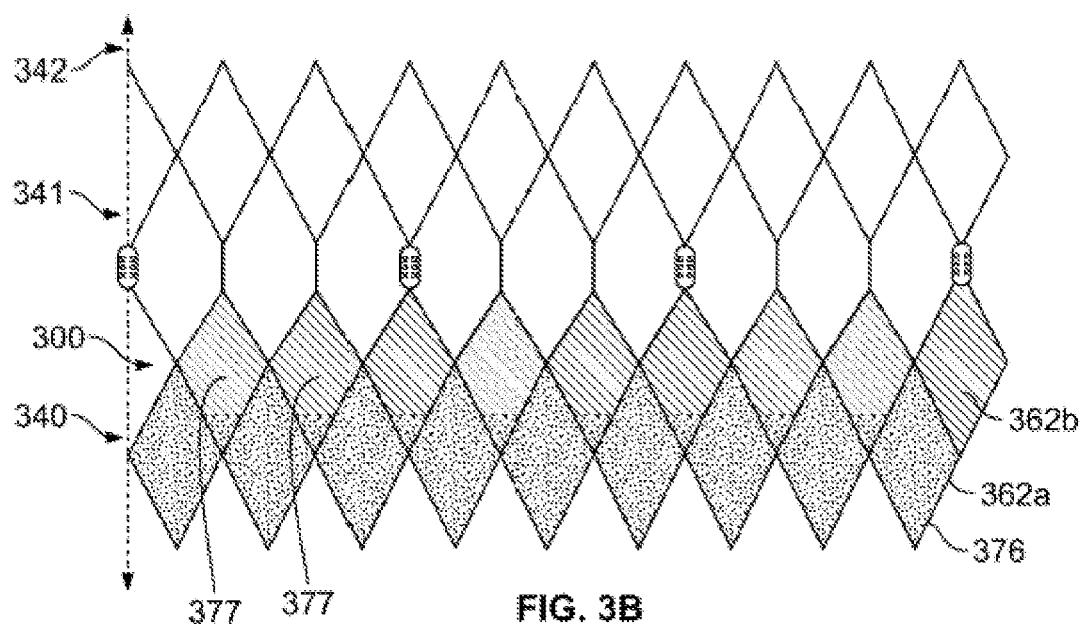
FIG. 3B is a developed view of a portion of the heart valve of FIG. 3A in an expanded condition.

Valve assembly 304, which includes circumferential cuff 376, may be disposed almost entirely within annulus section 340 as shown. In order to improve paravalvular sealing, cuff 376 is extended upward toward outflow end 332 compared to cuff 176 of prosthetic valve 100. As shown in FIG. 3A, the configuration of cuff 376 may result in potential gap space 200 being covered or eliminated, which may help mitigate PV leakage. In particular, as shown in FIG. 3B, stent 302 includes a plurality of rows of cells including a first annular row positioned at the inflow end and a second annular row adjacent the first annular row and closer to outflow end 332. Similar to heart valve 100, cuff 376 spans the entirety of each cell 362*a* in the first row. Unlike heart valve 100, cuff 376 also spans the entirety of each cell 362*b* in the second annular row. As indicated in FIG. 3B, potential gap space 200 is blocked by cuff 376. In addition, the additional cuff material may result in an increased likelihood that the cuff material wraps around any imperfections, such as calcified nodules, in the native leaflet, which may provide additional PV-leakage mitigation.

However, elongated or enlarging cuff 376 to cover potential gap space 200 may lead to a decrease in coronary perfusion by blocking coronary arteries 272. In particular, prosthetic heart valve 300 may be positioned such that at least a portion of one or more cells 362*b* in the second row is adjacent one or more coronary ostia or in contact with at least some amount of heart tissue defining the one or more coronary ostia. If prosthetic heart valve 300 is positioned in this manner, at least some portion of cuff 376, particularly portions of cuff 376 covering cells 362*b*, may obstruct blood from flowing into coronary arteries 272. These potentially blocking areas 377 of cuff 376 that may be positioned adjacent to or in contact with the coronary ostia are indicated with hashed lines in FIG. 3B. It should be understood that the size and position of areas 377 (if any) adjacent the coronary ostia may vary depending on the positioning of valve 300 within the patient's anatomy, as well as the anatomy itself.

Figure 4A:
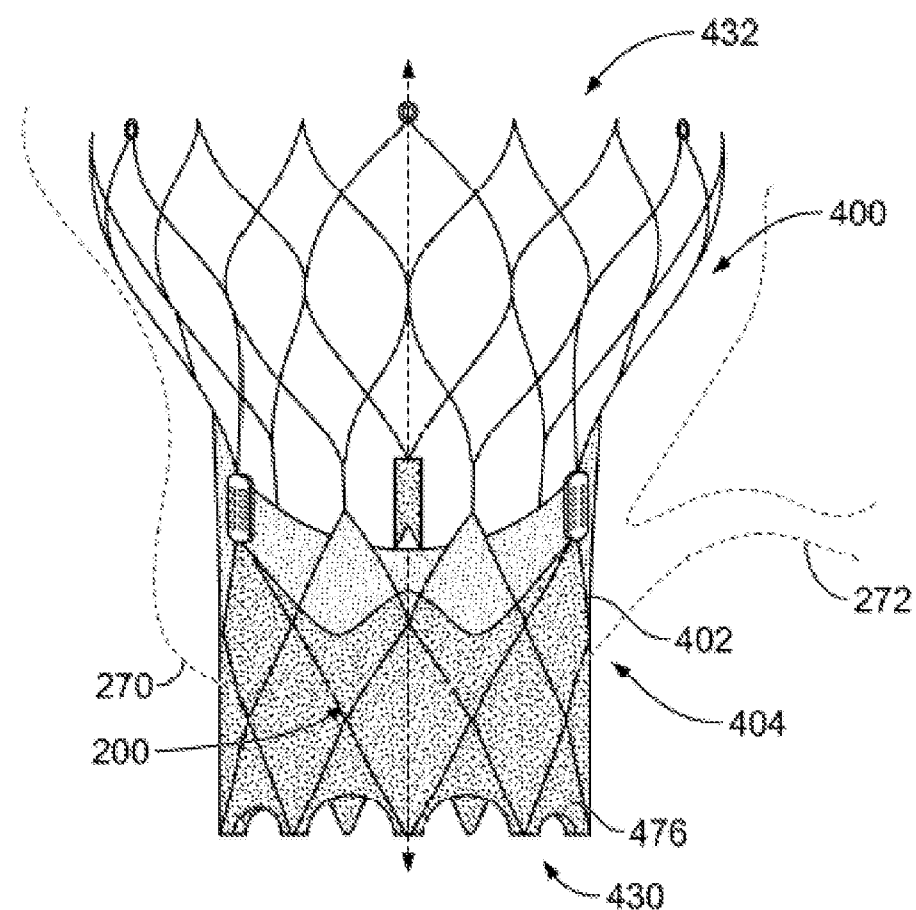
FIG. 4A is a side elevational view of a collapsible prosthetic heart valve of a further embodiment of the disclosure after implantation.

FIG. 4A illustrates another example of a collapsible stent-supported prosthetic heart valve 400 capable of reducing PV leakage. Generally, heart valve 400 may have similar features to heart valves 300 and 100. For example, heart valve 400 includes an expandable stent 402 extending from inflow end 430 to outflow end 432, with an annulus section 440 adjacent inflow end 430, an aortic section 442 adjacent outflow end 432, and a transition section 441 between annulus section 440 and aortic section 442. Prosthetic valve 400 may include a valve assembly 404 that, like valve assemblies 104 and 304, includes prosthetic leaflets and a cuff 476. However, unlike valve assemblies 104 and 304, an outflow end of cuff 476 of valve assembly 404, when in the expanded condition, extends generally along middle portions of cells of the stent. In other words, cuff 476 is positioned in a generally intermediate manner compared to the extended cuff configuration of cuff 376 and the relatively low cuff configuration of cuff 176.

Figure 4B:
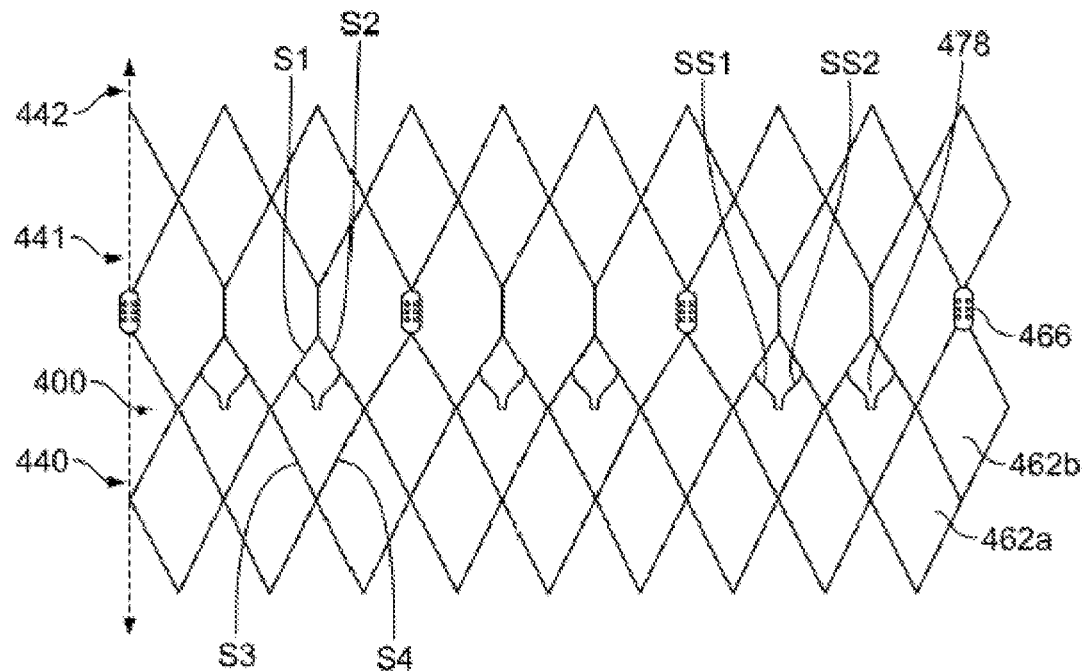
FIGS. 4B-4C are developed views of a portion of the heart valve of FIG. 4A in an expanded condition.
Figure 4C:
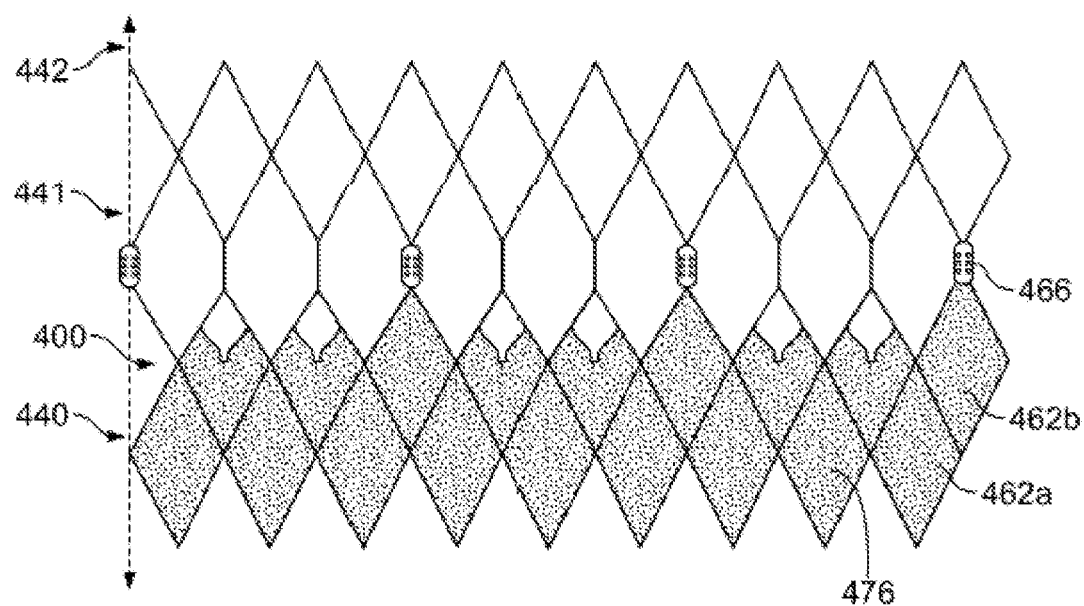

The structure of stent 402 that facilitates the above-described configuration of cuff 476 is illustrated in FIGS. 4B-C, which show developed views of a portion of heart valve 400. FIG. 4B illustrates stent 402 alone, while FIG. 4C illustrates stent 402 with cuff 476 attached. Stent 402 includes a plurality of rows of cells including a first annular row of cells 462*a* positioned at inflow end 430 and a second annular row of cells 462*b* adjacent the first annular row and closer to outflow end 432. Similar to heart valves 100 and 300, cuff 476 spans the entirety of each cell 462*a* in the first row. Unlike heart valves 100 and 300, however, cuff 476 spans the entirety of some cells 462*b* in the second annular row and less than the entirety of other cells 462*b* in the second annular row. Each cell 462*a*, 462*b* may be defined by a plurality of struts. For example, each cell 462*b* in the second row may be defined by four struts S1, S2, S3, and S4. Each strut S1-S4 may be substantially the same length. When stent 402 is in the expanded condition, struts S1 and S4 may be substantially parallel to (or may otherwise oppose) one another and struts S2 and S3 may be substantially parallel to (or may otherwise oppose) one another, struts S1-S4 forming a general diamond shape. Struts S1 and S2 may be positioned closer to outflow end 432 than struts S3 and S4.

Figure 4D:
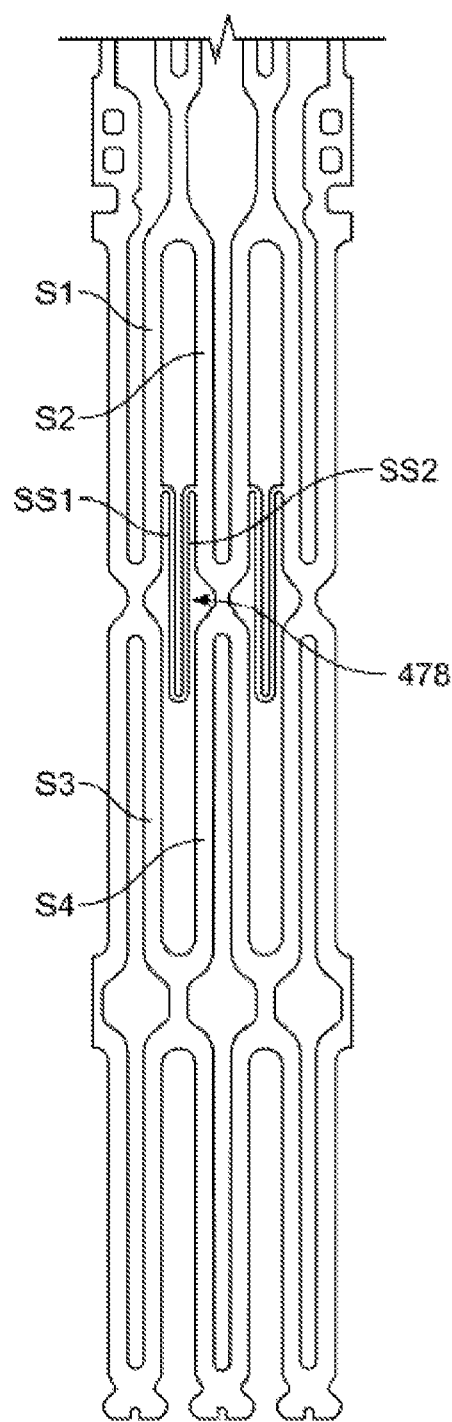
FIG. 4D is a developed view of a portion of the heart valve of FIG. 4A in a collapsed condition.

One or more cells 462*b* in the second row may include a bridging feature 478, which may be referred to as a "V"- shaped strut member, spanning from one of struts S1-S4 in the cell to another one of struts S1-S4 in the cell. Bridging feature 478 may be formed of a first supplemental strut SS1 and a second supplemental strut SS2, supplemental struts SS1 and SS2 each being substantially the same length and each being shorter than struts S1-S4. Supplemental struts SS1 and SS2 may be formed of the same material as struts S1-S4. In the illustrated embodiment, supplemental strut SS1 has a first end extending from a middle portion of strut S1 and a second end joining supplemental strut SS2. Supplemental strut SS2 has a first end joining supplemental strut SS1 and a second end extending to a middle portion of strut S2. Bridging feature 478 may have a valley or free end extending toward inflow end 430 of stent 402, formed by the connection of supplemental struts SS1 and SS2, so that the valley or free end is nested within cell 462b. With this configuration, bridging feature 478 may collapse as valve 400 is transitioned from the expanded condition to the collapsed condition, as shown in FIG. 4D. It should also be noted that the supplemental struts SS1 and SS2 may be generally thinner than other struts S1-S4 in stent 402, which may help minimize the force required to load the prosthetic valve 400 or resheath the valve 400 into a delivery device. In addition, the directionality of the bridging feature 478 (e.g. valley versus peak) may be chosen so that resheathing is not interrupted by, for example, the bridging feature 478 catching or hooking an end of the delivery device if the valve 400 is partially released and then resheathed back into the delivery device.

As best illustrated in FIGS. 4A and 4C, cuff 476 may be attached to stent 402 such that the outflow end of the cuff generally follows, and is attached to, bridging features 478 of stent 402, where present. In particular, cuff 476 may be attached to stent 402 at or near each commissure attachment feature 466, and then extend toward inflow end 430 along struts adjacent commissure attachment feature 466. Cuff 476 may extend across cells 462b with bridging features 478, being attached to supplemental struts SS1, SS2, such that selected edge portions of the outflow end of cuff 476 are coupled along the bridging features and to the valleys or free ends of the bridging features. In the illustrated embodiment, two cells 462b with bridging features 478 circumferentially follow cell 462b without a bridging feature, the cell 462b without a bridging feature having a commissure attachment feature 466 at one end thereof. Because prosthetic heart valve 400 is designed for use with a prosthetic valve having three leaflets, stent 402 includes three repeating series of cells 462b as described above, corresponding to the three leaflets. However, it should be understood that other patterns may be suitable for attaching the outflow end of cuff 476 across intermediate portions of cells of a stent, whether for use with a three-leaflet valve, or a valve with more or fewer leaflets. Also, it should be understood that, although stent 402 is described as being formed of a plurality of struts, stent 402 may be created as an integral structure, for example by laser cutting a tube of Nitinol.

The configuration of cuff 476, with its outflow end extending across intermediate portions of certain cells 462b of the second annular row, may facilitate coronary perfusion while still mitigating PV leakage. For example, because cuff 476 is positioned to cover at least a portion of cells 462b of the second annular row, the potential gap space 200 is covered, as illustrated in FIG. 4A. However, because an upper or outflow portion of most cells 462b in the second annular row remains uncovered by cuff 476, there is less likelihood that blood will be obstructed from flowing into coronary arteries 272 by cuff 476. Essentially, attaching cuff 476 along bridging features 478 of stent 402 preserves the coronary perfusion benefits of valve 100 and the PV leak mitigation benefits of valve 300 as they relate to the positioning of the respective cuffs.

The exact positioning and number of bridging features 478 may vary from that described above. For example, supplemental struts SS1 and SS2 may extend from strut S3 to strut S4, rather than from strut S1 to strut S2. Alternately, supplemental struts SS1 and SS2 may extend from the point at which strut S1 connects to strut S3 to the point at which strut S2 connects to strut S4. In addition, although bridging features 478 are illustrated with a valley extending toward inflow end 430, the configuration may be reversed such that bridging features 478 include a peak extending toward outflow end 432, which may be particularly useful to facilitate resheathing depending on the mode of delivery. Supplemental struts SS1 and SS2 may be shape-set so that, in the absence of applied force, they extend radially outwardly from the cell in which they are positioned. In other words, when the stent is in the expanded condition, the cell defines a surface and the supplemental struts SS1 and SS2 extend radially outwardly from that surface. In this configuration, upon deployment of valve 400, bridging features 478 and portions of cuff 476 attached to bridging features 478 may be biased radially outward to create a better seal between valve 400 and the native tissue, further mitigating potential PV leakage. That is, if any gap space exists between the deployed stent 402 and native valve annulus 250, bridging features 478 and the portions of cuff 476 attached thereto may extend radially outwardly to fill that space. In addition, although bridging features 478 are described as being positioned in a second circumferential row of cells, the concepts apply to other types of stents with more or fewer rows. For example, in a stent with a high-density arrangement of cells (i.e. more cells per unit area), bridging features may be positioned within a third, fourth, or other rows of cells, depending on the intended position of the stent in relation to the native anatomy.

In one embodiment of the disclosure, a prosthetic heart valve comprises:

a stent having a collapsed condition and an expanded condition and extending from an inflow end to an outflow end, the stent including: a first circumferential row of cells defined by a first plurality of struts; a second circumferential row of cells defined by a second plurality of struts, the second circumferential row being positioned closer to the outflow end of the stent than the first circumferential row, at least one cell in the second circumferential row including a first strut opposed to a fourth strut and a second strut opposed to a third strut, the first and fourth struts being connected to the second and third struts; a bridging feature in at least one cell in the second circumferential row, the bridging feature including a first supplemental strut having a first end and a second end, and a second supplemental strut having a first end and a second end, the first end of the first supplemental strut being attached to at least one of the first and third struts, the second end of the first supplemental strut being attached to the first end of the second supplemental strut, and the second end of the second supplemental strut being attached to at least one of the second and fourth struts; and a cuff having an inflow end and an outflow end, the outflow end of the cuff being coupled to the stent along the bridging feature; and/or the first end of the first supplemental strut is attached to the first strut, and the second end of the second supplemental strut is attached to the second strut; and/or the second end of the first supplemental strut and the first end of the second supplemental strut together form a valley pointing toward the inflow end of the stent; and/or the one cell defines a surface, and the first and second supplemental struts extend radially outwardly from the surface in the absence of applied forces when the stent is in the expanded condition; and/or the cuff fully covers at least one cell in the first circumferential row; and/or the cuff fully covers at least one cell in the second circumferential row; and/or at least two adjacent cells in the second circumferential row include the bridging feature; and/or at least two adjacent cells in a first group of cells in the second circumferential row include the bridging feature and at least two adjacent cells in a second group of cells in the second circumferential row include the bridging feature, the first group of cells and the second group of cells being separated by at least one cell without the bridging feature; and/or a first portion of the one cell is covered so as to prevent blood from flowing therethrough and a second portion of the one cell is open so as to allow blood to flow therethrough, the first portion being positioned closer to the inflow end of the stent than the second portion; and/or the prosthetic heart valve is configured to be positioned within a native valve annulus so that a portion of the first circumferential row of cells is in contact with the native valve annulus and a portion of the second circumferential row of cells is adjacent a coronary artery ostium.

In another embodiment of the disclosure, a method of implanting a prosthetic heart valve into a native valve annulus comprises: providing a prosthetic heart valve including a stent and a cuff attached to the stent, the stent extending from an inflow end to an outflow end and having a collapsed condition, an expanded condition, a first circumferential row of cells, and a second circumferential row of cells, the cuff having an outflow end attached to at least one bridging feature extending across an intermediate portion of at least one of the cells in the second circumferential row; delivering the prosthetic heart valve to a site of implantation in the collapsed condition; and deploying the prosthetic heart valve at the site of implantation, wherein, when the stent is in the expanded condition, a portion of the first circumferential row of cells is in contact with the native valve annulus and a portion of the second circumferential row of cells is adjacent a coronary artery ostium; and/or the at least one cell with the bridging feature includes a first strut opposed to a fourth strut and a second strut opposed to a third strut, the first and fourth struts being connected to the second and third struts, and the bridging feature in the at least one cell includes a first supplemental strut having a first end and a second end, and a second supplemental strut having a first end and a second end, the first end of the first supplemental strut being attached to at least one of the first and third struts, the second end of the first supplemental strut being attached to the first end of the second supplemental strut, and the second end of the second supplemental strut being attached to at least one of the second and fourth struts; and/or the first end of the first supplemental strut is attached to the first strut, and the second end of the second supplemental strut is attached to the second strut; and/or the second end of the first supplemental strut and the first end of the second supplemental strut together form a valley pointing toward the inflow end of the stent; and/or the one cell defines a surface, and the first and second supplemental struts extend radially outwardly from the surface in the absence of applied forces when the stent is in the expanded condition; and/or the cuff fully covers at least one cell in the first circumferential row; and/or the cuff fully covers at least one cell in the second circumferential row; and/or at least two adjacent cells in the second circumferential row include the bridging feature; and/or at least two adjacent cells in a first group of cells in the second circumferential row include the bridging feature and at least two adjacent cells in a second group of cells in the second circumferential row include the bridging feature, the first group of cells and the second group of cells being separated by at least one cell without the bridging feature; and/or a first portion of the one cell is covered so as to prevent blood from flowing therethrough and a second portion of the one cell is open so as to allow blood to flow therethrough, the first portion being positioned closer to the inflow end of the stent than the second portion.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims. For example, features described in relation to one embodiment described above may be combined with features of another embodiment described above without departing from the scope of the invention.

The invention claimed is:

1. A prosthetic heart valve, comprising:
a stent having a collapsed condition and an expanded condition and extending from an inflow end to an outflow end, the stent having a plurality of rows of cells extending around a circumference of the stent, each cell formed by a plurality of cell struts, selected cells including a bridging feature, each bridging feature including a first supplemental strut and a second supplemental strut, first ends of the first and second supplemental struts being coupled to cell struts of a respective selected cell, a second end of the first supplemental strut coupled to a second end of the second supplemental strut to form a free end of the bridging feature nested within the respective selected cell;
a valve assembly disposed within the stent; and
a cuff having an inflow end and an outflow end, selected edge portions of the outflow end of the cuff being coupled to the stent along the bridging features and to the free ends,
wherein the selected cells each define a surface, and each bridging feature extends radially outward of a corresponding one of the surfaces in the absence of applied forces.

2. The prosthetic heart valve of claim 1, wherein the bridging features are "V"-shaped.

3. The prosthetic heart valve of claim 1, wherein the second ends of the first and second supplemental struts of each bridging feature together form a valley pointing toward the inflow end of the stent.

4. The prosthetic heart valve of claim 1, wherein the plurality of rows of cells include a first row of cells and a second row of cells adjacent the first row of cells, the first row of cells being positioned nearer the inflow end of the stent than is the second row of cells.

5. The prosthetic heart valve of claim 4, wherein the cuff fully covers at least one cell in the first row of cells.

6. The prosthetic heart of claim 4, wherein the cuff fully covers at least one cell in the second row of cells.

7. The prosthetic heart valve of claim 4, wherein at least two adjacent cells in the second row of cells include the bridging features.

8. The prosthetic heart valve of claim 4, wherein at least two adjacent cells in a first group of cells in the second row of cells include the bridging features and at least two adjacent cells in a second group of cells in the second row of cells include the bridging features, the first group of cells and the second group of cells being separated by at least one cell without the bridging feature.

9. The prosthetic heart valve of claim 1, wherein a first portion of one of the selected cells is covered so as to prevent blood from flowing therethrough and a second portion of the one of the selected cells is open so as to allow blood to flow therethrough, the first portion being positioned closer to the inflow end of the stent than the second portion.

10. The prosthetic heart valve of claim 1, wherein each bridging feature has a collapsed condition in the collapsed condition of the stent and an expanded condition in the expanded condition of the stent, the collapsed condition of each bridging feature being different than the expanded condition of each bridging feature.

11. The prosthetic heart valve of claim 1, wherein the selected cells are diamond shaped.

12. The prosthetic heart valve of claim 1, wherein the selected cells include a first strut and a second strut joined together at a first apex pointing toward the outflow end of the stent, and a third strut and a fourth strut joined together at a second apex pointing toward the inflow end of the stent.

13. The prosthetic heart valve of claim 12, wherein the first ends of the first supplemental struts are coupled to corresponding ones of the first struts and the first ends of the second supplemental struts are coupled to corresponding ones of the second struts.

14. The prosthetic heart valve of claim 12, wherein the first ends of the first and second supplemental struts are positioned nearer the first apex than the second apex.

15. The prosthetic heart valve of claim 1, wherein the selected edge portions of the outflow end of the cuff are positioned radially outward of corresponding ones of the surfaces in the absence of applied forces.

16. The prosthetic heart valve of claim 1, wherein the cuff is positioned on a luminal surface of the stent.

17. The prosthetic heart valve of claim 1, wherein the cuff is positioned on an abluminal surface of the stent.

18. The prosthetic heart valve of claim 1, wherein the cuff is positioned on a luminal surface of the stent and an abluminal surface of the stent.

19. A prosthetic heart valve, comprising:
a stent having a collapsed condition and an expanded condition and extending from an inflow end to an outflow end, the stent having a plurality of rows of cells extending around a circumference of the stent, each cell formed by a plurality of cell struts, selected cells including a "V"-shaped strut member coupled to cell struts of the selected cells, each "V"-shaped strut member defining a free end nested within a corresponding one of the selected cells;
a valve assembly disposed within the stent; and
a cuff having an inflow end and an outflow end, selected edge portions of the outflow end of the cuff being coupled to the stent along the "V"-shaped strut members and to the free ends, wherein the selected cells each define a surface, and, for each selected cell, portions of the "V"-shaped strut member extend radially outward of the surface in the absence of applied forces so that the selected edge portions of the outflow end of the cuff are positioned radially outward of the surfaces in the absence of applied forces.

* * * * *